(12) United States Patent
Delgado

(10) Patent No.: US 12,414,726 B2
(45) Date of Patent: Sep. 16, 2025

(54) APPARATUS FOR EARLY DETECTION OF CARDIAC AMYLOIDOSIS

(71) Applicant: Reynolds Delgado, Houston, TX (US)

(72) Inventor: Reynolds Delgado, Houston, TX (US)

( * ) Notice: Subject to any disclaimer, the term of this patent is extended or adjusted under 35 U.S.C. 154(b) by 221 days.

(21) Appl. No.: 17/828,937

(22) Filed: May 31, 2022

(65) Prior Publication Data

US 2022/0386928 A1 Dec. 8, 2022

Related U.S. Application Data

(60) Provisional application No. 63/196,416, filed on Jun. 3, 2021.

(51) Int. Cl.
| | |
|---|---|
| A61B 5/318 | (2021.01) |
| A61B 5/28 | (2021.01) |
| A61B 5/335 | (2021.01) |
| A61B 5/339 | (2021.01) |
| A61B 5/352 | (2021.01) |
| A61B 5/353 | (2021.01) |
| A61B 5/36 | (2021.01) |

(52) U.S. Cl.
CPC ............. *A61B 5/36* (2021.01); *A61B 5/28* (2021.01); *A61B 5/335* (2021.01); *A61B 5/339* (2021.01); *A61B 5/352* (2021.01); *A61B 5/353* (2021.01)

(58) Field of Classification Search
CPC ................... A61B 5/352; A61B 5/353
See application file for complete search history.

(56) References Cited

U.S. PATENT DOCUMENTS

| 5,400,796 | A | 3/1995 | Wecke | |
|---|---|---|---|---|
| 2010/0318026 | A1* | 12/2010 | Grunwald | A61M 25/0097 604/95.05 |
| 2011/0196248 | A1* | 8/2011 | Grunwald | A61B 5/339 600/509 |
| 2012/0136242 | A1* | 5/2012 | Qi | A61B 8/5223 604/95.01 |
| 2014/0276162 | A1* | 9/2014 | Albert | A61B 5/316 600/509 |

OTHER PUBLICATIONS

PCT Search Report.

* cited by examiner

*Primary Examiner* — Eric D. Bertram
(74) *Attorney, Agent, or Firm* — Eric P. Mirabel

(57) ABSTRACT

An improved wearable device for detecting progression of Cardiac Amyloidosis based on changes in relative values of characteristics of P-wave and R-wave is disclosed. In an embodiment of the invention, two electrodes the device are connected to user's skin surface to obtain traces of ECG signals. Thereafter, correction factors are determined for the obtained traces of ECG signals. A microprocessor included in the device applies correction factors on the traces of ECG signals to obtain characteristics of P-wave and R-wave. Finally, the microprocessor determines the ratio of the characteristics (such as amplitude) of the P-wave to the characteristics (such as amplitude) of the R-wave and records said ratio. Still further, the microprocessor compares all such recorded ratios or features, to determine and display if there is disease progression.

8 Claims, 5 Drawing Sheets

APPARATUS FOR EARLY DETECTION OF CARDIAC AMYLOIDOSIS

BACKGROUND

Amyloidosis is a group of diseases in which abnormal proteins, known as amyloid fibrils, build up in tissue. There are several types with varying symptoms. Typical symptoms may include diarrhea, weight loss, feeling tired, enlargement of the tongue, bleeding, numbness, feeling faint while standing, swelling of the legs, or enlargement of the spleen.

In cardiac amyloidosis, amyloid deposition in the heart can cause both diastolic and systolic heart failure. Cardiac amyloidosis can present with symptoms of heart failure including shortness of breath, fatigue, and edema. As cardiac amyloidosis progresses, the amyloid deposition can affect the heart's ability to pump and can lead to premature atrial contractions as well as reduce its ability to maintain normal rhythm, which leads to worsening heart function and decline in quality of life.

Progressive reduction in QRS amplitude with progressive increase in left ventricular thickness is well-known as being associated with cardiac amyloidosis CA. It is also well known that R-wave amplitude declines as the disease progresses. Grading scales and predictive models based on the R-wave amplitude decline have been proposed. It is less well accepted that P-wave amplitude and duration (width) increases as well with disease progression. These P-wave changes are likely the result of bi-atrial enlargement caused by restrictive cardiomyopathy. Furthermore, atrial amyloid deposition itself delays atrial conduction and thereby increases the PR interval and widens the P-wave.

To diagnose or model cardiac amyloidosis using a 12 lead EKG, one can start with the Sokolow-Lyon criteria have been widely used for diagnosing left ventricular hypertrophy (LVH) in patients with hypertension. The Sokolow-Lyon criteria indicates LVH if the S-wave depth in V1+ tallest R-wave height in V5–V6>35 mm to reduce the effects of significant artifacts, often present in the 12 lead EKG plots. Artifacts associated with the 12 lead ECG would not be a problem where absolute value is not necessary, but where one measures only the relative values of the R-wave to the P-wave, or another set of parameters where absolute R and P-wave values are not relied upon.

Moreover, the absolute value of the R-wave cannot be accurately determined with a wearable device (such as an Apple Watch or the KardiaMobile EKG Monitor) because it changes with electrical current conduction and related factors, including differences in skin-electrode interface impedances, body morphology, adhesion of the electrode, perspiration by the patient, and other differences. U.S. Pat. No. 6,950,694 (incorporated by reference) discusses that where only two electrodes are used, the ECG signal obtained between the first and second electrodes is also typically severely degraded by common-mode noise signals, such as 60 Hertz or other environmental noise signals that is present at both the first and second electrodes. Because of the high input-impedance of the instrumentation amplifier, even small differences in the skin-electrode impedance (e.g., 10 kilo-ohms) can result in a common-mode noise signal amplitude that exceed the amplitude of the desired ECG signal.

Thus, what is needed is a reliable testing device for providing early detection and surveillance for cardiac amyloidosis (before a patient becomes symptomatic), which can preferably be used conveniently and often by the patients themselves. Such a self-administered test need not require a 12 lead EKG or echocardiogram and instead would be platformed on a wearable device, having only two electrodes.

SUMMARY

It is an object of the present invention to provide a testing device (preferably a wearable device) which does not require measurement of the absolute value of the R-wave (because of its wide inherent variability) and facilitates early detection and surveillance for cardiac amyloidosis.

Progression of cardiac amyloidosis, without measurement of the absolute value of the R-wave, can be done by determining a change in the relative value (which can be expressed e.g. as a ratio) of the features of the R-wave with respect to the features of the P-wave over a period of time. For example, a decreasing relative value of the R-wave amplitude with respect to the P-wave amplitude over time indicates a progression in disease. Similarly monitoring other ratios of features of the R and P-wave (including wave durations) can also indicate disease progression. For example, an increasing interval between the P-wave and the R-wave can also indicate disease progression.

Specifically, the features of the P-wave and R-wave which can be expressed as relative values or ratios, and then compared over time to indicate disease onset or progression, more accurately and reliably, include:
  (i) the P-wave area and the R-wave amplitude;
  (ii) the P-wave duration and the R-wave amplitude;
  (iii) the P-wave amplitude and duration (preferably expressed as a sum or product of those values) compared with the R-wave amplitude;
  (iv) the ratio of the P-wave amplitude to a function (including the sum) of R and the S-wave amplitude; and
  (v) the ratio of the P-wave area to a function (including the sum) of the R and the S-wave amplitude.

An increasing ratio of one or more of the above ratios (i.e., i-v) indicates an increase in disease progression. Among the listed ratios, the ratios iv and v are particularly important because these ratios provide a measure of electrical activity of the heart independent of its ECG axis. This eliminates the variations in measurement of heart activity due to differences in ECG axis between individuals. Additionally, an increasing interval between the P-wave and the R-wave can also indicate disease progression.

None of the above comparisons require reliance on the absolute value of the R-wave. The relative values can be expressed as ratios of features of the P-wave with respect to the R-wave (or functions, including sums, of the R and the S-wave), and then compared over time to determine disease onset or progression. The comparisons and ratios can be initiated at various times including at early disease stages. This ratio(s) can readily be measured, recorded and/or displayed on a wearable device.

In one aspect, the invention provides a reliable testing device (preferably, a wearable device) which facilitates early detection and surveillance for cardiac amyloidosis by determining a change in the relative ratio of the amplitude of the R-wave with respect to the amplitude of the P-wave over a period of time. According to an embodiment of the present invention, the testing device is a wearable device for determining and comparing the ratio of the P-wave amplitude to the R-wave amplitude. The device includes:
  at least one first lead with a first electrode adapted to contact a first portion of a user's skin surface;

at least one second lead with a second electrode adapted to contact a second portion of a user's skin surface; said first and second leads are connected to a patient's body to generate an ECG trace of the amplitude of the user's P-wave and R-wave; and a microprocessor adapted to determine the ratio of the amplitudes and to record said ratio and further capable of for comparison of the ratio to subsequently measured ratios.

In another aspect, the invention provides a reliable testing device (preferably, a wearable device) which facilitates early detection and surveillance for cardiac amyloidosis by determining a change in the relative value of the area of the P-wave to the amplitude of the R-wave over a period of time. According to an embodiment of the present invention, the testing device is a wearable device for determining and comparing the ratio of the area of the P-wave and the amplitude of the R-wave. The device comprises:

at least one first lead with a first electrode adapted to contact a first portion of a user's skin surface;

at least one second lead with a second electrode adapted to contact a second portion of a user's skin surface; said first and second leads are connected to a patient's body to generate an ECG trace of the area of the P-wave and the amplitude of the R-wave; and a microprocessor adapted to determine the ratio of the area of the P-wave and the amplitude of the R-wave, and to record said relative values and further capable of comparison of the ratio to subsequently measured relative values.

In another aspect, the invention provides a reliable testing device (preferably, a wearable device) which facilitates early detection and surveillance for cardiac amyloidosis by determining a change in the relative value of the duration of the P-wave to the amplitude of the R-wave over a period of time. According to an embodiment of the present invention, the testing device is a wearable device for determining and comparing the ratio of the duration of the P-wave and the amplitude of the R-wave. The device includes:

at least one first lead with a first electrode adapted to contact a first portion of a user's skin surface;

at least one second lead with a second electrode adapted to contact a second portion of a user's skin surface; said first and second leads are connected to a patient's body to generate an ECG trace of the duration of the P-wave and the amplitude of the R-wave; and a microprocessor adapted to determine the ratio of the duration of the P-wave and the amplitude of the R-wave, and to record said relative values and further capable of comparison of the ratio to subsequently measured relative values.

In another aspect, the invention provides a reliable testing device (preferably, a wearable device) which facilitates early detection and surveillance for cardiac amyloidosis by determining a change in the relative value of either of the sum of the amplitude and duration of the P-wave and the amplitude of the R-wave amplitude, or the product of the amplitude and duration of the P-wave and the amplitude of the R-wave over a period of time. According to an embodiment of the present invention, the testing device is a wearable device for determining and comparing the value of the sum of the amplitude and duration of the P-wave and the amplitude of the R-wave amplitude, or the product of the amplitude and duration of the P-wave and the amplitude of the R-wave, including:

at least one first lead with a first electrode adapted to contact a first portion of a user's skin surface;

at least one second lead with a second electrode adapted to contact a second portion of a user's skin surface;

said first and second leads are connected to a patient's body to generate an ECG trace of the amplitude of the user's R-wave and the amplitude and the duration of user's P-wave; and a microprocessor adapted to determine the ratio of one of:
i) sum of the amplitude and duration of the P-wave, and the amplitude of the R-wave amplitude, and
ii) product of the amplitude and duration of the P-wave, and the amplitude of the R-wave; and
to record said relative values and further capable of comparison to subsequently measured relative values.

In another aspect, the invention provides a reliable testing device (preferably, a wearable device) which facilitates early detection and surveillance for cardiac amyloidosis by determining a change in the relative value of the amplitude of the P-wave to a function of the amplitudes of the R-wave and the S-wave over a period of time. According to an embodiment of the present invention, the testing device is a wearable device for determining and comparing the ratio of the amplitude of the P-wave to a function of amplitudes of the R-wave and the S-wave, wherein the function can be the sum of the amplitudes of the R-wave and the S-wave, comprising:

at least one first lead with a first electrode adapted to contact a first portion of a user's skin surface;

at least one second lead with a second electrode adapted to contact a second portion of a user's skin surface;

said first and second leads are connected to a patient's body to generate an ECG trace of the amplitudes of the P-wave, the R-wave and the S-wave; and a microprocessor adapted to determine the ratio of the amplitude of the P-wave to the sum of amplitudes of the R-wave and the S-wave, and to record said relative values and further capable of comparison to subsequently measured relative values.

In another aspect, the invention provides a reliable testing device (preferably, a wearable device) which facilitates early detection and surveillance for cardiac amyloidosis by determining a change in the relative value of the area of the P-wave to a function of amplitudes of the R-wave and the S-wave over a period of time. According to an embodiment of the present invention, the testing device is a wearable device for determining and comparing the ratio of the area of the P-wave to a function of the amplitudes of the R-wave and the S-wave, wherein the function can be the sum of the amplitudes of the R-wave and the S-wave, comprising:

at least one first lead with a first electrode adapted to contact a first portion of a user's skin surface;

at least one second lead with a second electrode adapted to contact a second portion of a user's skin surface;

said first and second leads are connected to a patient's body to generate an ECG trace of the P-wave, the R-wave and the S-wave; and a microprocessor adapted to determine the ratio of the area of the P-wave to a function of the amplitudes of the R-wave and the S-wave, wherein the function can be the sum of the R-wave and the S-wave amplitudes, and to record said relative values and further capable of comparison to subsequently measured relative values.

In another aspect, the invention provides a reliable testing device (preferably, a wearable device) which facilitates early detection and surveillance for cardiac amyloidosis by determining a change in the interval between the P-wave and the R-wave over a period of time. As increasing interval between the P-wave and the R-wave indicates disease progression. According to an embodiment of the present invention, the testing device is a wearable device for determining and comparing a change in the interval between the P-wave and the R-wave, comprising:

at least one first lead with a first electrode adapted to contact a first portion of a user's skin surface;

at least one second lead with a second electrode adapted to contact a second portion of a user's skin surface;

said first and second leads are connected to a patient's body to generate an ECG trace of the P-wave, the R-wave (and optionally the S-wave); and a microprocessor adapted to determine the interval between the P-wave and the R-wave and to record said interval and further capable of comparison to subsequently measured intervals.

Further details and embodiments of the present invention will be discussed in greater detail with reference to the accompanying figures in the detailed description which follows.

DETAILED DESCRIPTION

Progression of cardiac amyloidosis, without measurement of the absolute value of the R-wave, can be done by determining a change in the relative value (which can be expressed e.g. as a ratio) of the features of the R-wave with respect to the features of the P-wave over a period of time. For example, a decreasing relative value of the R-wave amplitude with respect to the P-wave amplitude over time indicates a progression in disease. Similarly monitoring other ratios of features of the R and P-wave (including wave intervals) can also indicate disease progression. For example, an increasing interval between the P-wave and the R-wave can also indicate disease progression.

Figure 1:
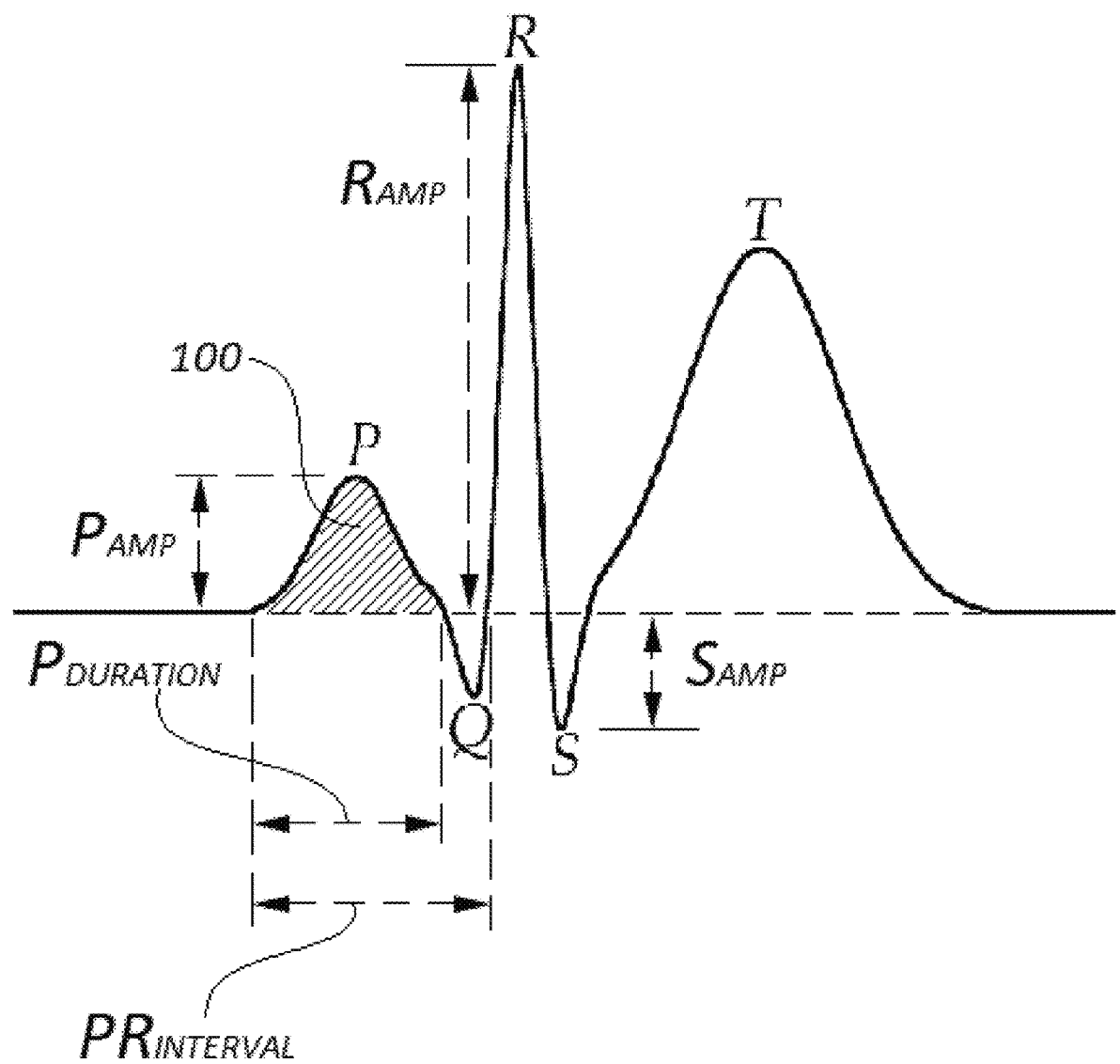
FIG. 1 illustrates an ECG signal.

FIG. 1 illustrates a common ECG signal. In the illustrated ECG signal '$R_{AMP}$' is the amplitude of the R-wave, '$P_{AMP}$' is the amplitude of the P-wave, '$S_{AMP}$' is the amplitude of the S-wave, '$P_{DURATION}$' is the duration of the P-wave, '$PR_{INTERVAL}$' is the interval between the of the P-wave and the R-wave, and shaded area 100 is the area of P-wave.

Specifically, the characteristics of the P-wave and R-wave which can be expressed as relative values or ratios, and then compared over time to indicate disease onset or progression, more accurately and reliably, include:

(i) the P-wave area and the R-wave amplitude;
(ii) the P-wave duration and the R-wave amplitude;
(iii) the P-wave amplitude and duration (preferably expressed as a sum or product of those values) compared with the R-wave amplitude;
(iv) the ratio of the P-wave amplitude to a function (including the sum) of the R and the S-wave amplitude; and
(v) the ratio of the P-wave area to a function (including the sum) of the R and the S S-wave amplitude.

An increasing ratio of one or more of the above ratios (i.e., i-v) indicates an increase in disease progression. Among the listed ratios, the ratios iv and v are particularly important because these ratios provide a measure of electrical activity of the heart independent of the ECG axis. This eliminates the variations in measurement of heart activity due to differences in the ECG axis between individuals. Additionally, an increasing interval between the P-wave and the R-wave can also indicate disease progression.

None of the above comparisons require reliance on the absolute value of the R-wave. The relative values can be expressed as ratios of features of the P-wave with respect to the R-wave (or the R and the S-wave), and then compared over time to determine disease onset or progression. The comparisons and functions can be initiated at various times including at early disease stages. This values can readily be measured, recorded and/or displayed on a wearable device.

A feature of the preferred wearable device is that it is equipped with circuitry, such as filters, for providing features of the P and the R-waves. Characteristics such as frequency, amplitude, and time interval of only P and R-waves are made available for analysis and comparison, and artifacts which are external to the P and the R-waves are filtered out. Such filtering increases the reliability of the determinations of the relative values of features of the R-wave with respect to the P-wave.

Further details regarding the wearable device, the filtering and use of signal post-processing to correct distortions are described below.

Figure 2:
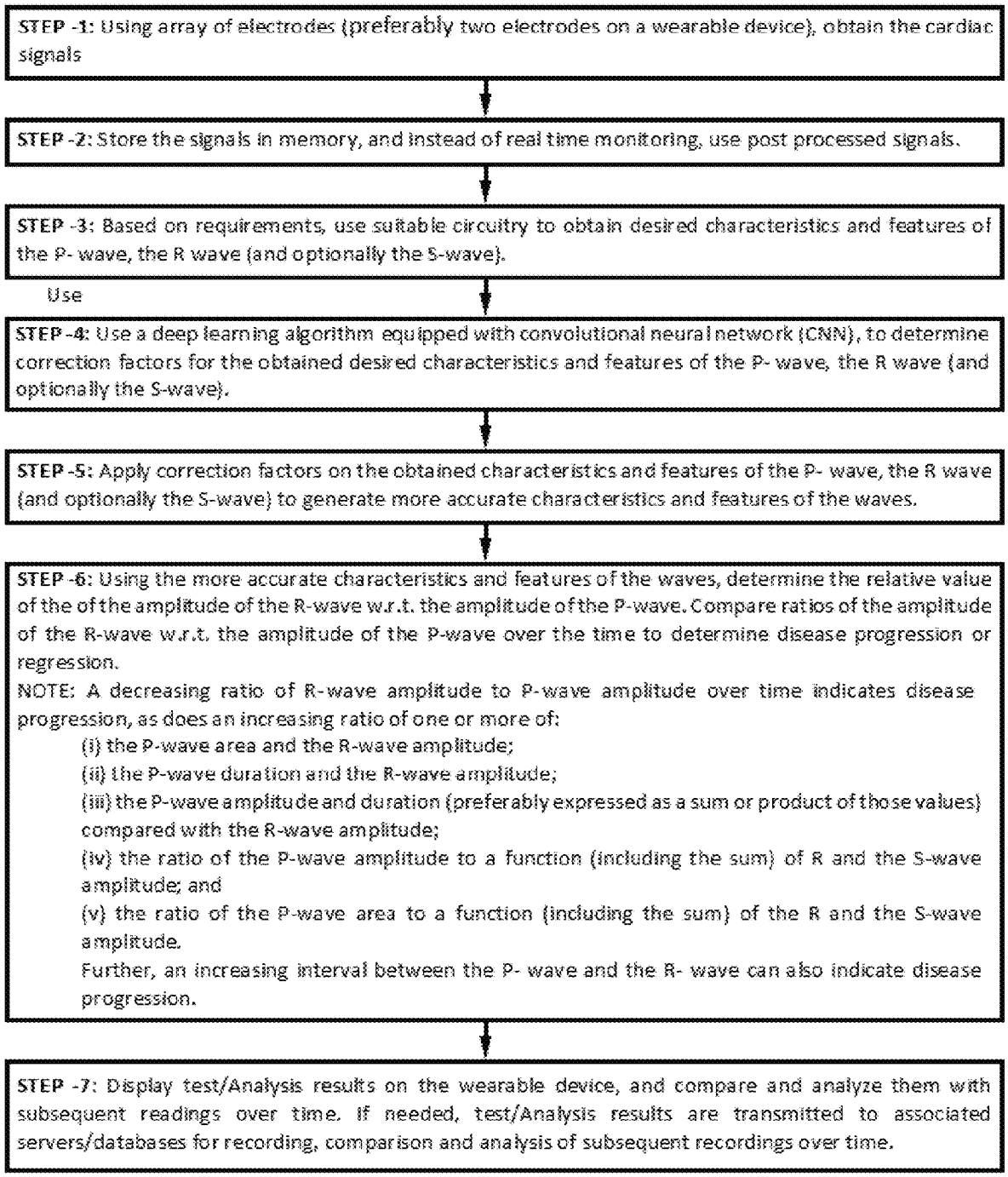
FIG. 2 is a flow chart showing the steps in a method of amyloidosis detection executed by a device of the invention.

FIG. 2 is a flow chart showing the steps followed by a testing device (preferably, a wearable device) for detecting of progression of cardiac amyloidosis in accordance with the present invention.

As illustrated, in step-1 cardiac signals (i.e. ECG) are obtained by using and array of electrodes (preferably, two electrodes on a wearable device).

In step-2, obtained cardiac signals are stored in a memory. Instead of real time monitoring, the stored signals are preferably post processed signals.

In step-3, based on requirements, suitable circuitry is used to obtain desired characteristics or features of the P-wave and the R-wave (or the P-wave, the R-wave the S-wave).

In step-4, a deep learning algorithm equipped with convolutional neural network (CNN), is used to determine correction factors for the desired characteristics and features of the P-wave and the R-wave (or the P-wave, the R-wave and the S-wave).

In step-5, the correction factors are applied on the obtained characteristics or features of the P-wave and the R-wave (or the P-wave, the R-wave the S-wave) to generate more accurate characteristics or features of the waves.

In step-6, the generated more accurate characteristics or features of the waves are used to determine the relative value of the of the amplitude of the R-wave w.r.t. the amplitude of the P-wave. Thereafter, ratios of the amplitude of the R-wave w.r.t. amplitude of the P-wave generated over time are compared to determine disease progression. It is to be noted that a decreasing ratio of amplitude of the R-wave to the amplitude of the P-wave over the time indicates disease progression.

In other embodiments of the invention, a change in following ratios can also be used to detect disease progression. An increasing ratio of one or more of the following indicates disease progression:
  (i) the P-wave area to the R-wave amplitude;
  (ii) the P-wave duration to the R-wave amplitude;
  (iii) the P-wave amplitude and duration (preferably expressed as a sum or product of those values) to the R-wave amplitude;
  (iv) the ratio of the P-wave amplitude to a function (including the sum) of the R and the S-wave amplitude; and
  (v) the ratio of the P-wave area to a function (including the sum) of the R and the S-wave amplitude.

Still further, an increasing interval between the P-wave and the R-wave can also indicate disease progression.

Finally, in step-7, Test/Analysis results are displayed on a display screen of the wearable device, and are then compared as subsequent readings are generated. If needed, results may also be transmitted to an associated servers/databases for recording and comparison and analysis of subsequent recordings over time.

In one aspect, the invention provides a reliable testing device (preferably, a wearable device) which facilitates early detection and surveillance for cardiac amyloidosis by determining a change in the relative value of the amplitude of the R-wave with respect to the amplitude of the P-wave over a period of time.

In another aspect, the invention provides a reliable testing device (preferably, a wearable device) which facilitates early detection and surveillance for cardiac amyloidosis by determining a change in the relative value of the duration of the P-wave to the amplitude of the R-wave.

In yet another aspect, the invention provides a reliable testing device (preferably, a wearable device) which facilitates early detection and surveillance for cardiac amyloidosis by determining a change in the relative value of either of the sum of the amplitude and duration of the P-wave and the amplitude of the R-wave amplitude, or the product of the amplitude and duration of the P-wave and the amplitude of the R-wave over a period of time.

In yet another aspect, the invention provides a reliable testing device (preferably, a wearable device) which facilitates early detection and surveillance for cardiac amyloidosis by determining a change in the relative value of the amplitude of the P-wave to a function (which can be a sum) of the amplitudes of the R-wave and the S-wave over a period of time.

In yet another aspect, the invention provides a reliable testing device (preferably, a wearable device) which facilitates early detection and surveillance for cardiac amyloidosis by determining a change in the relative value of the area of the P-wave to a function (which can be a sum) of the of amplitudes of the R-wave and the S-wave over a period of time.

In yet another aspect, the invention provides a reliable testing device (preferably, a wearable device) which facilitates early detection and surveillance for cardiac amyloidosis by determining a change in the interval between the P-wave and the R-wave over a period of time. An increasing interval between the P-wave and the R-wave can also indicate disease progression.

Reference will now be made in detail to a first embodiment of the invention with reference to the accompanying FIGS. 3 and 4.

Figure 3:
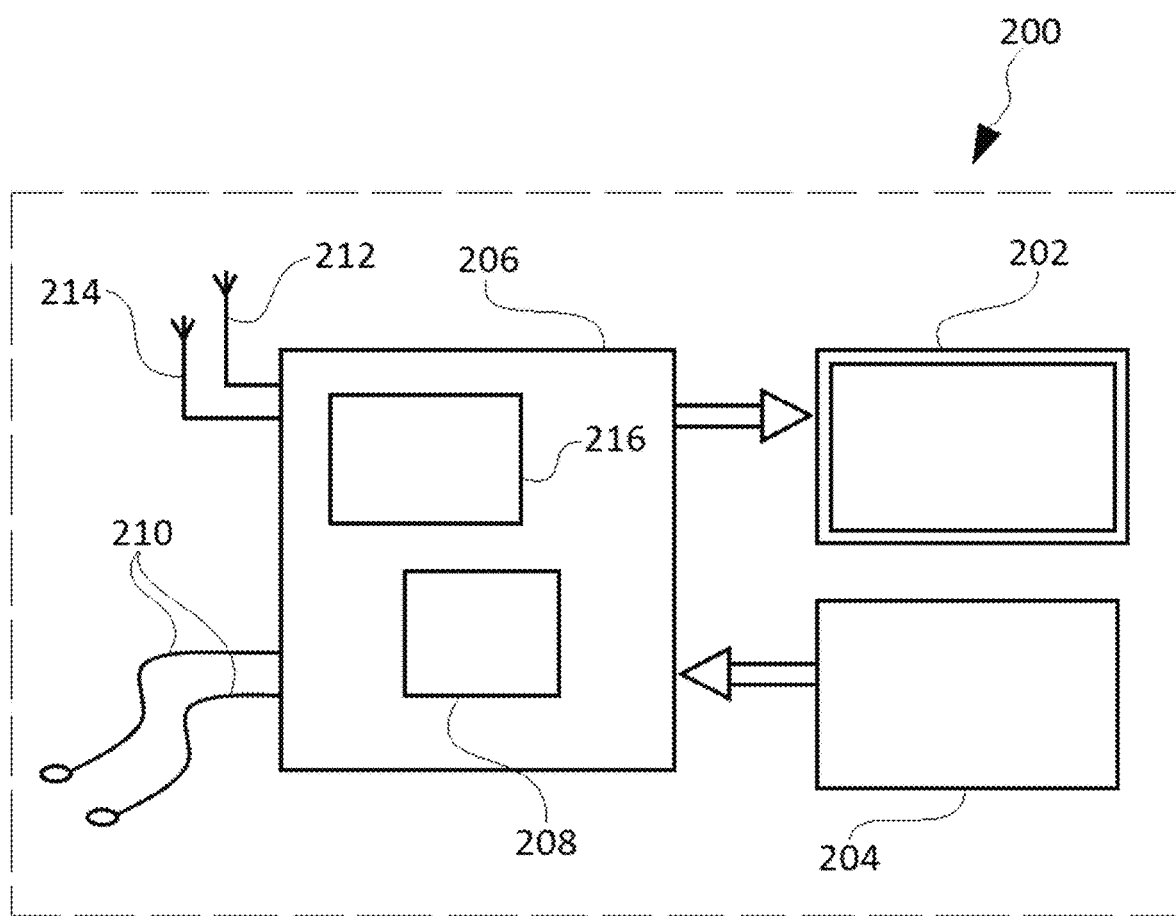
FIG. 3 is a structural block diagram of a first embodiment of a wearable device for detecting of Cardiac Amyloidosis in accordance with the present invention.
Figure 4:
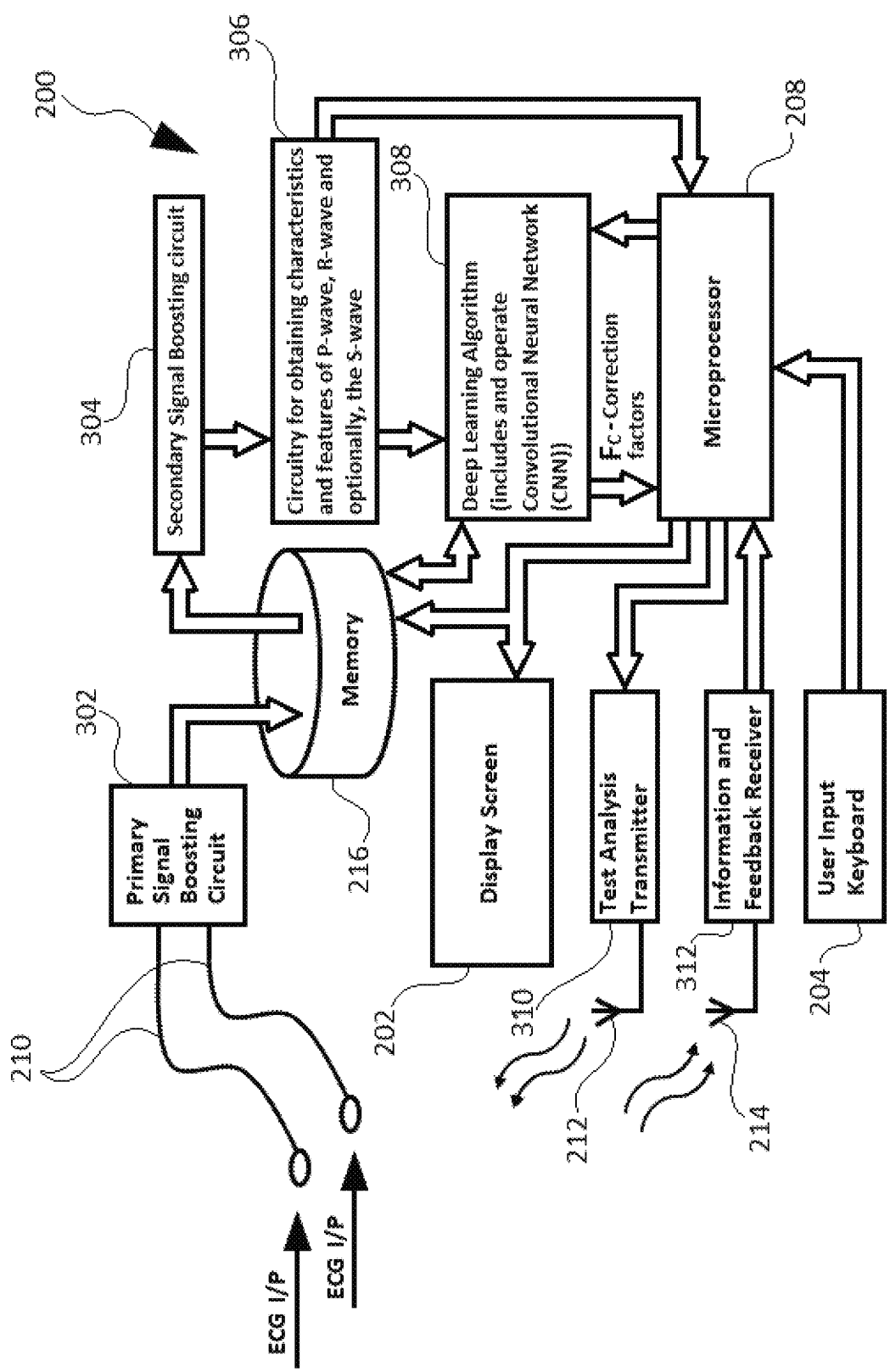
FIG. 4 is a detailed block diagram of a first embodiment of a wearable device of FIG. 3.
Figures 5A, 5B, 5C, 5D:
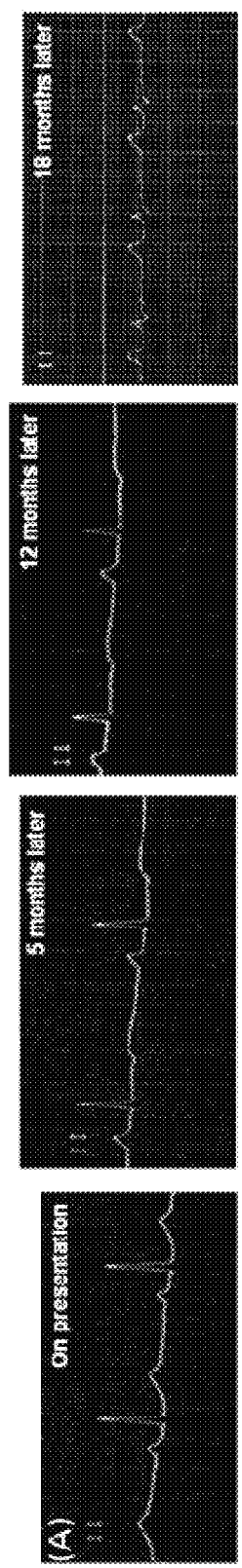
FIGS. 5A to 5D illustrate electrocardiograms of a patient from a baseline in FIG. 5A, at then respectively at intervals of five months, twelve months and eighteen months in FIGS. 5B to 5D, and indicating progression of cardiac amyloidosis over such period.

FIG. 3 illustrates a structural block diagram of components of a first embodiment of a testing device (i.e. a wearable device 200) for detection of progression of cardiac amyloidosis in accordance with present invention. As illustrated, the wearable device 200 includes a display screen 202, a user input keyboard 204, a circuit board (or motherboard) 206, a microprocessor 208 (included in the motherboard 206), a memory 216 (also included in the circuit board 206), two electrode leads 210, a transmitter antenna 212 and a receiver antenna 214. The wearable device 200 (and all its illustrated components) are powered by DC supply i.e. a rechargeable battery (not shown).

A detailed explanation of the process of detection of progression of cardiac amyloidosis by wearable device 200 will now be explained with reference to FIG. 4 which illustrates a detailed block diagram of the wearable device 200. As illustrated in FIG. 4, the circuitry of wearable device 200 includes a primary signal boosting circuit 302, a secondary signal boosting circuit 304, circuitry for obtaining characteristics of the P, R and optionally the S-wave 306, embedded software circuitry hosting a deep learning algorithm (which includes and operates a convolution neural network (CNN) 308), microprocessor 208, memory 216, display screen 202, test analysis transmitter circuit 310, Information and feedback receiver circuit 312, a transmitter antenna 212, a receiver antenna 214 and two electrode leads 210.

The primary signal boosting circuit 302, secondary signal boosting circuit 304, circuitry for obtaining characteristics of the P, R and optionally the S-wave 306, embedded software circuitry hosting a deep learning algorithm (which includes and operates a convolution neural network (CNN) 308), test analysis transmitter circuit 310, and information and feedback receiver circuit 312 are all placed on the motherboard 206 (illustrated in FIG. 3).

For detection of progression of cardiac amyloidosis, the two electrode leads 210 are connected to a patient's skin surface and the wearable device 200 is powered-on. Preferably on the basis of the user input provided from keyboard 204, the two electrode leads 210 generate an ECG trace of the P-wave, and the R-wave (and optionally, the S-wave) at predefined durations. The duration of mentioned predefined durations may be set as per requirements by the user through the input keyboard 204. The generated ECG traces are boosted through primary signal boosting circuit 302 and are stored in memory 216. The user can determine the status of progression of cardiac amyloidosis by activating the processor 208 (e.g., using the keyboard 204), to execute an instruction set (similar to the one illustrated in FIG. 2) and provide an output indicating the results of progression of cardiac amyloidosis on a display screen (such as on LCD display screen 202). In detail, the processor 208 causes a retrieval of the P-wave, the R-wave (and optionally, the S-wave) signals stored in the memory 216, and re-boosts them through secondary signal boosting circuit 304. Thereafter, the boosted signals are passed through circuitry 306 for obtaining characteristics and features of the P-wave, and the R-wave (and optionally, the S-wave). Once the desired characteristics and features of the mentioned waves are obtained (for example, the amplitudes, areas, duration etc. of the P-wave, R-wave and S-wave) the obtained characteristics are passed on to the embedded software circuitry hosting a deep learning algorithm (which includes and operates a convolution neural network (CNN) 308) to obtain correction factors Fc. Thereafter, the correction factors Fc are applied to the selected features of the P-wave, and the R-wave (and optionally, the S-wave) to generate a more accurate representation of the features of the waves. In the following step, the corrected features of the P-wave, and the R-wave (and optionally, the S-wave) are used to determine the relative value (or the ratio) of the R-wave (or the R-wave and the S-wave) features with respect to ("wrt") the P-wave features. In the next step, based on obtained relative value or ratio based on comparison with previously stored features, the progression of cardiac amyloidosis is detected. For example, a decreasing ratio of R-wave amplitude to P-wave amplitude over time indicates disease progression. Finally, the analysis and detected results are displayed on the wearable device, and if desired, are also transmitted to associated servers/databases for recording, comparison and further analysis. While wireless transmission of data from wearable device 200 is done through transmitter circuit 310 and a transmitter antenna 212, wireless reception of data from wearable device 200 is done through information and feedback receiver circuit 312 and a receiver antenna 214.

As amyloid protein deposits in the heart, a decreasing R-wave amplitude reflects the decreasing electrical conductance of the myocardium. FIGS. 5A to 5D illustrate repeat electrocardiograms of the same patient over 18 months. These tracings are taken from: Leeson et al., "Atrial pathology in cardiac amyloidosis: evidence from ECG and cardiovascular magnetic resonance," European Heart Journal, Volume 27, Issue 14, 1670-(2006)) (incorporated by reference). The illustrated electrocardiograms show a progressive reduction in amplitude of the QRS voltage; and concomitantly, a marked increase in P-wave width and amplitude, and lengthening of the PR-wave interval.

In electrocardiograms illustrated in of FIGS. 5A to 5D, the R to P-wave amplitude ratio of the same patient decrease over time from 6-to-4-to-2-to-1, indicating disease progression over 18 months. Because the changes in the R to P (or P to R) amplitude ratio can be determined using wearable devices, disease can be conveniently detected in its early stages, leading to earlier treatment and better outcomes. In the last few years treatments have been developed for both AL and TTR amyloid, the two most common types, and a potential cure for AL is being studied currently. With early detection and treatment commencement, disease progression may be effectively inhibited. Because of the convenience and portability of the wearable device, this method of detection can also be used conveniently for long term real time surveillance of disease initiation in otherwise normal subjects.

While the first embodiment of the invention has been explained by monitoring the ratio of the amplitudes of the R-wave and the P-wave, the following features of the R-wave and P-wave can also be compared to detect progression of cardiac amyloidosis:

(i) the P-wave area to the R-wave amplitude;
(ii) the P-wave duration to the R-wave amplitude;
(iii) the P-wave amplitude and duration (preferably expressed as a sum or product of those values) to the R-wave amplitude;
(iv) the ratio of the P-wave amplitude to a function (including a summation) of the R wave and S-wave amplitudes; and
(v) the ratio of the P-wave area to a function (including a summation) of the R wave and S-wave amplitudes.

It is to be noted that an increase in any of the ratios (i)-(v) indicate disease progression. Still further, an increasing interval between the P-wave and the R-wave can also indicate disease progression.

In a second embodiment of the invention, the testing device is a wearable device, which is structurally similar to wearable device 200 of the first embodiment as described above, and that monitors a change in ratio of the area of the P-wave to the amplitude of the R-wave over time. An increasing ratio indicates progression of cardiac amyloidosis.

In a third embodiment of the invention, the testing device is a wearable device, which is structurally similar to wearable device 200 of the first embodiment as described above, and that monitors a change in ratio of the duration of the P-wave and the amplitude of the R-wave over time. An increasing ratio indicates progression of cardiac amyloidosis.

In a fourth embodiment of the invention, the testing device is a wearable device, which is structurally similar to wearable device 200 of the first embodiment as described above, and that monitors a change of ratio of either the sum or the product of the amplitude and duration of the P-wave with the amplitude R-wave over period of time. An increasing ratio indicates progression of cardiac amyloidosis.

In a fifth embodiment of the invention, the testing device is a wearable device, which is structurally similar to wearable device 200 of the first embodiment as described above, and monitors a change in ratio of the amplitude of the P-wave to a feature (including the sum) of the amplitudes of the R-wave and the S-wave over time to. An increasing ratio indicates progression of cardiac amyloidosis.

In a sixth embodiment of the invention, the testing device is a wearable device, which is structurally similar to wearable device 200 of the first embodiment as described above, and monitors a change in ratio of the area of the P-wave a feature (including the sum) of the amplitudes of the R-wave and the S-wave over time t. An increasing ratio indicates progression of cardiac amyloidosis.

In a seventh embodiment of the invention, the testing device is a wearable device, which is structurally similar to wearable device 200 of the first embodiment as described above, and determines a change in the interval between the P-wave and the R-wave over time. An increasing interval indicates progression of cardiac amyloidosis.

In an ECG, the P-wave varies in frequency from 0.67-5 Hz and the QRS-wave from 10-50 Hz. The common frequencies of the artifact and noise on the ECG: muscle: 5-50 Hz; respiratory: 0.12-0.5 Hz; external electrical: 50 or 60 Hz (A/C frequency); other electrical: typically >10 Hz (muscle stimulators, strong magnetic fields, pacemakers with impedance monitoring).

The skin-electrode interface typically is a highly significant source of interference, as it produces a DC component of 200-300 mV— compared with the electrical activity of the heart, which is only in the range of 0.1 to 2 mV. The interference at the skin-electrode interface is significantly magnified by motion, including patient movement, electrode movement and even movement resulting from respiratory variation. Thus, all these sources of interference should be filtered to improve readability and reliability of the R and P-wave signals. depending on which P and R-wave features are being compared or monitored.

Moreover, phase shifts can be significant in two electrode touch pad ECGs, and such phase shifts can significantly affect the P-wave to R-wave duration and frequency. Correcting for phase shifts can require a different type of filtering.

A filter can also be included that filters out premature ventricular contractions PVCs and/or premature atrial contractions (PACs), or other common cardiac events which produce interference.

Four common types of ECG filtering are: high-pass, low-pass (bandpass), notch, and common mode filtering. The notch filter is used to eliminate the line frequency and is usually printed on the ECG (e.g. ~60 Hz). Common mode rejection is often done by sending an inverse signal of the other three limb electrodes back through the right leg electrode.

Real time filter outputs tend to distort different frequencies differently, thereby causing phase distortion. In the event one is measuring the P to R-wave duration to determine disease progression, or the duration of the P-wave, this phase distortion would significantly affect the reliability of the results. One solution is to do signal post processing rather than real time monitoring of the signals; as post-processing does not generate phase distortion.

The post signal processing can be guided by determining appropriate correction factors to correct distortions or differences in the skin electrode results vs. the regular multi-lead ECG tracing of the difference in P and R-wave amplitudes; the P-wavelength and area under it; as well as the P to R-wave duration. The correction factors can be readily determined by using a deep learning algorithm fitted over a training set (representing many subjects) of skin electrode results and regular multi-lead ECG tracings, each taken from the same subject. See V. Jindal et al., "An Adaptive Deep Learning Approach for PPG-Based Identification" IEEE pp. 6401-04 (2016) (incorporated by reference).

Correction factors to accurately determine the difference in the P and R-wave amplitudes, and to accurately reflect the P-wavelength and area under it as well as the P to R-wave duration can be extracted using an unsupervised deep learning algorithm. The training set can be used to find one or more correction factors by fitting to the training set with a deep learning algorithm. See V. Jindal et al., supra. A preferred deep learning algorithm is a convolutional neural network (CNN), which given a large amount of data, can learn deep (several layers) and discriminate representations and classifiers directly from the data itself. Other suitable deep learning algorithms include a deep neural network ("DNN"), long short-term memory recursive neural network ("LSTM-RNN"), or a Convolutional, Long Short-Term Memory Deep Neural Network ("CL-DNN").

The features of the R-wave and the P-wave used in the validation sets are similar to those in the test sets. That is, for example, one or more of: the difference in the P and R-wave amplitudes, the P-wavelength and area under it, the P to R-wave duration, each taken at the same time from the same subject, as determined using a regular ECG tracing. The validation set is used to tune the hyperparameters of the classifier and avoid overfitting, e.g., by using the validation set for regularization. In one simple example, regularization is by early stopping of training, when the error on the validation dataset increases, as this is a sign of overfitting to the training dataset. Overfitting can also be reduced by using dropout, which regularizes the objective function by randomly setting a certain percentage of nodes in the neural network to zero (ignoring them) during training.

Suitable wearable devices include those with two inputs and two skin surface contacts, such as described in WO2016116918 (incorporated by reference), which discusses a two finger pressable electrode pad device for capturing data indicative of at least one electrical signal of the patient's heart; a housing portion comprising at least one ECG analog front end (ECG-AFE) for recording the signal; at least two filter circuit means for filtering out background noise and frequency interference; digital signal processing unit (DSP) for transmitting at least one signal; and, a wireless communication means for transmitting results.

Other modifications in the embodiments of the present invention to enhance results include data augmentation, which can be generated by changing the scale, or changing the attenuation or gain of particular R-waves, by a specified percentage. J. da Silva Luz et al., supra.

The signal features or values are then classified, as in Choi et al., "Biometric Authentication Using Noisy Electrocardiograms Acquired by Mobile Sensors" IEEE pp. 1266-73 (2016) (incorporated by reference), by an appropriate one-class classifier, where a one-class Support Vector Machine (SVM) classifier is preferred, but can also include: Naïve-Bayes; Logistic Regression, Support Vector Machine, Bayesian Network, Multilayer Perceptron, Deep Neural Networks, RBF Network, Bagging, Random Forest and Adaboost. Choi et al. designed a cascading bandpass filter for noise cancellation and suggested eight fiducial features. For classification-based authentication, they used the radial basis function kernel-based support vector machine, which showed the best performance among nine classifiers through experimental comparison. Upon classification, the chosen one-class machine learning algorithm will determine if the input function or values matches those in the database. Those that do not match may be measured again.

When a subject's readings are determined from a portable or wearable device (such as one having a two lead touch pad sensor) this AI-based method would provide post-processing correction factors which could be used to ensure reliability of parameters of the R and the P-waves (such as amplitude, the P-wave length and area under it, as well as the P to R-wave duration) and their relative value with respect to each other In addition to application in a wearable device, this method of determining disease progression could also be incorporated in other medical devices such as a home blood pressure monitoring and recording device (equipped with appropriate hardware and software), as it simply requires a two lead ECG. It could also be incorporated into heart rate detectors incorporated in exercise machines, where each lead terminates in an electrode which is part of a hand grip for one hand, or even to a car steering wheel; as one only needs contact by both hands on two separate electrodes. In other embodiments, it could be a stand alone device for home use or use in a clinic or pharmacy. As noted, all such devices can also be equipped with wireless transmitters to relay data for external collection and/or signal processing (for example, at a server).

The embodiments, components, steps, features, objects, benefits, and advantages which have been discussed are merely illustrative, and not limiting. All articles, patents, patent applications, and other publications that have been cited in this disclosure are incorporated herein by reference. Relational terms such as "first" and "second" and the like may be used solely to distinguish one entity or action from another, without necessarily requiring or implying any actual relationship or order between them. The terms "comprises," "comprising," "including" and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type. The invention is defined only in the claims which follow and includes all equivalents of the elements in the claims.

What is claimed is:

1. A device for determining and comparing the amplitude of the P-wave to a function of the amplitudes of the R-wave and the S-wave, comprising:

at least one first lead with a first electrode adapted to contact a first portion of a user's skin surface;

at least one second lead with a second electrode adapted to contact a second portion of a user's skin surface;

said first and second leads are connected to a patient's body to generate an ECG trace of the user's P-wave, S-wave and R-wave; and a microprocessor adapted to determine a ratio of the amplitude of the P-wave to a function consisting of the amplitudes of the R-wave and the S-wave, and to record said ratio for comparison to said ratio subsequently measured, and said microprocessor is also adapted to compare said ratio recorded at a first time to said ratio determined and recorded at one or more later times, and to provide notification of a progression of cardiac amyloidosis to a display screen if said ratio changes over time.

2. The device of claim 1, wherein said ratio is a summation ratio of the amplitude of the P-wave to a sum of amplitudes of the R-wave and the S-wave.

3. The device of claim 1 wherein the display screen is part of a wearable device.

4. The device of claim 1 wherein the device includes a user input keyboard.

5. The device of claim 1 wherein the device includes two electrode leads.

6. The device of claim 1 wherein the device includes a transmitter antenna and a receiver antenna.

7. The device of claim 1 wherein the device includes a rechargeable battery.

8. The device of claim 1 wherein the device includes a filter adapted to filter out premature ventricular contractions and/or premature atrial contractions, or other common cardiac events which produce interference.

\* \* \* \* \*